(12) United States Patent
Ushio et al.

(10) Patent No.: US 8,375,745 B2
(45) Date of Patent: Feb. 19, 2013

(54) PROCESS FOR PRODUCING CELL ELECTROPHYSIOLOGICAL SENSOR AND APPARATUS FOR PRODUCING THE CELL ELECTROPHYSIOLOGICAL SENSOR

(75) Inventors: Hiroshi Ushio, Osaka (JP); Masaya Nakatani, Hyogo (JP); Makoto Takahashi, Osaka (JP)

(73) Assignee: Panasonic Corporation, Osaka (JP)

( * ) Notice: Subject to any disclaimer, the term of this patent is extended or adjusted under 35 U.S.C. 154(b) by 244 days.

(21) Appl. No.: 12/808,499

(22) PCT Filed: Nov. 28, 2008

(86) PCT No.: PCT/JP2008/003510
§ 371 (c)(1),
(2), (4) Date: Jun. 16, 2010

(87) PCT Pub. No.: WO2009/081521
PCT Pub. Date: Jul. 2, 2009

(65) Prior Publication Data
US 2011/0126590 A1   Jun. 2, 2011

(30) Foreign Application Priority Data

Dec. 20, 2007  (JP) ................................ 2007-328344
Jul. 29, 2008  (JP) ................................ 2008-194473

(51) Int. Cl.
*C03B 23/043*  (2006.01)
*C03B 23/09*   (2006.01)
(52) U.S. Cl. ............................................. 65/57; 65/36
(58) Field of Classification Search ............. 65/57, 59.2, 65/174
See application file for complete search history.

(56) References Cited

U.S. PATENT DOCUMENTS

| | | | | |
|---|---|---|---|---|
| 2,867,948 A | * | 1/1959 | Zimmerman | 65/40 |
| 3,632,325 A | * | 1/1972 | Evey et al. | 65/56 |
| 2009/0081765 A1 | | 3/2009 | Nakatani et al. | |
| 2009/0178922 A1 | * | 7/2009 | Nakatani et al. | 204/403.01 |
| 2009/0236224 A1 | * | 9/2009 | Yamasato et al. | 204/415 |
| 2009/0281410 A1 | * | 11/2009 | Ushio et al. | 600/395 |

FOREIGN PATENT DOCUMENTS

| | | |
|---|---|---|
| CN | 101127316 A | 2/2008 |
| JP | 2007-174990 A | 7/2007 |
| JP | 2007-174990 A | 7/2007 |
| JP | 2008-047696 A | 2/2008 |
| WO | WO 99/66329 A1 | 12/1999 |
| WO | WO 2007/119772 A1 | 10/2007 |
| WO | WO 2007/119772 A1 | 10/2007 |
| WO | WO 2008004476 A1 * | 1/2008 |

OTHER PUBLICATIONS

International Search Report for Application No. PCT/JP2008/003510, Jan. 13, 2009, Panasonic Corporation.

* cited by examiner

*Primary Examiner* — Matthew Daniels
*Assistant Examiner* — Cynthia Szewczyk
(74) *Attorney, Agent, or Firm* — RatnerPrestia

(57) ABSTRACT

A process including holding sensor chip; holding glass tube surrounding the outer periphery of the side surface of sensor chip; applying a wind pressure to the side surface of glass tube from the outside of glass tube and melting glass tube to be glass-welded to the side surface of sensor chip. Thereby, the outer periphery of sensor chip can be surrounded by a highly hydrophilic glass tube. Thus, a cell electrophysiological sensor with high measurement accuracy can be produced.

8 Claims, 6 Drawing Sheets

PROCESS FOR PRODUCING CELL ELECTROPHYSIOLOGICAL SENSOR AND APPARATUS FOR PRODUCING THE CELL ELECTROPHYSIOLOGICAL SENSOR

THIS APPLICATION IS A U.S. NATIONAL PHASE APPLICATION OF PCT INTERNATIONAL APPLICATION PCT/JP2008/003510.

TECHNICAL FIELD

The present invention relates to a production process of a cell electrophysiological sensor that can be used for an analysis of a pharmacological reaction of a cell and the like, and to a production apparatus of the cell electrophysiological sensor.

BACKGROUND ART

A patch clamp technique in electrophysiology is known as a method for measuring an ion channel that is present in a cell membrane. With this patch clamp technique, various functions of the ion channel have been elucidated. The function of the ion channel is of keen interest in cytology and is applied to development of drugs.

Meanwhile, however, a measuring method by the patch clamp technique requires an extremely high skill of inserting a fine micropipette into one cell with high accuracy. Therefore, this technique requires a skilled operator, so that it is not suitable for cases that require high-throughput measurement.

Therefore, an automated system that does not require the insertion of a micropipette into an individual cell and is capable of automatically fixing and measuring a cell merely by reducing a pressure has been developing.

As shown in FIG. 9, a conventional cell electrophysiological sensor includes mounting substrate 1 made of resin, sensor chip 3 that is made of silicon and inserted into through hole 2 of mounting substrate 1, and electrodes 4 and 5 disposed on the upper and lower parts of mounting substrate 1.

Furthermore, sensor chip 3 has conducting hole 6. Electrolytic bath 7 disposed inside through hole 2 of mounting substrate 1 and on mounting substrate 1 and electrolytic bath 8 disposed at the lower part are filled with an electrolytic solution. Electrolytic baths 7 and 8 are partitioned by mounting substrate 1 and sensor chip 3.

In this cell electrophysiological sensor, cell 9 is filled in electrolytic bath 7. Cell 9 can be sucked and trapped in an opening part of conducting hole 6 by applying a pressure from the upper part or reducing a pressure from the lower part of conducting hole 6. Then, for example, a drug is provided from the upper part of cell 9, and the potential difference between electrolytic baths 7 and 8 is measured by electrodes 4 and 5. Thus, the pharmacological reaction of cell 9 can be determined (see, for example, Patent Document 1).

Conventional sensor chip 3 has a problem that the measurement accuracy of the cell electrophysiological sensor is low. The reason therefor is that air bubbles 10 tend to be deposited in the vicinity of conducting hole 6 of sensor chip 3.

That is to say, as shown in FIG. 9, a conventional cell electrophysiological sensor is produced by directly inserting sensor chip 3 into mounting substrate 1 and fixing it with, for example, an adhesive agent. In the cell electrophysiological sensor, the outer periphery of sensor chip 3 is surrounded by the inner wall of through hole 2 of mounting substrate 1. Since mounting substrate 1 is hydrophobic, air bubbles tend to be deposited inside through hole 2. When air bubbles are deposited in the vicinity of conducting hole 6 of sensor chip 3, the adhesion between cell 9 and an opening part of conducting hole 6 is reduced or continuity between the upper and lower parts of conducting hole 6 is prevented. As a result, the measurement accuracy of the cell electrophysiological sensor is reduced.

[Patent Document 1] Japanese Translation of PCT Publication No. 2002-518678

SUMMARY OF THE INVENTION

The present invention has an object to produce a cell electrophysiological sensor having high measurement accuracy.

The present invention includes a step of holding a sensor chip, a step of holding a glass tube surrounding an outer periphery of a side surface of the sensor chip, and a step of applying a wind pressure to the side surface of the glass tube from the outside of the glass tube and melting the glass tube to be glass-welded to the side surface of the sensor chip.

Thus, the present invention can produce a cell electrophysiological sensor having high measurement accuracy. That is to say, according to the present invention, the outer periphery of the sensor chip can be surrounded by a highly hydrophilic glass tube. Therefore, it is possible to produce a cell electrophysiological sensor in which air bubbles are not likely to be generated in the vicinity of the sensor chip. As a result, a cell electrophysiological sensor in which air bubbles are not likely to be deposited in the vicinity of the conducting hole and which has high measurement accuracy.

Figure 1:
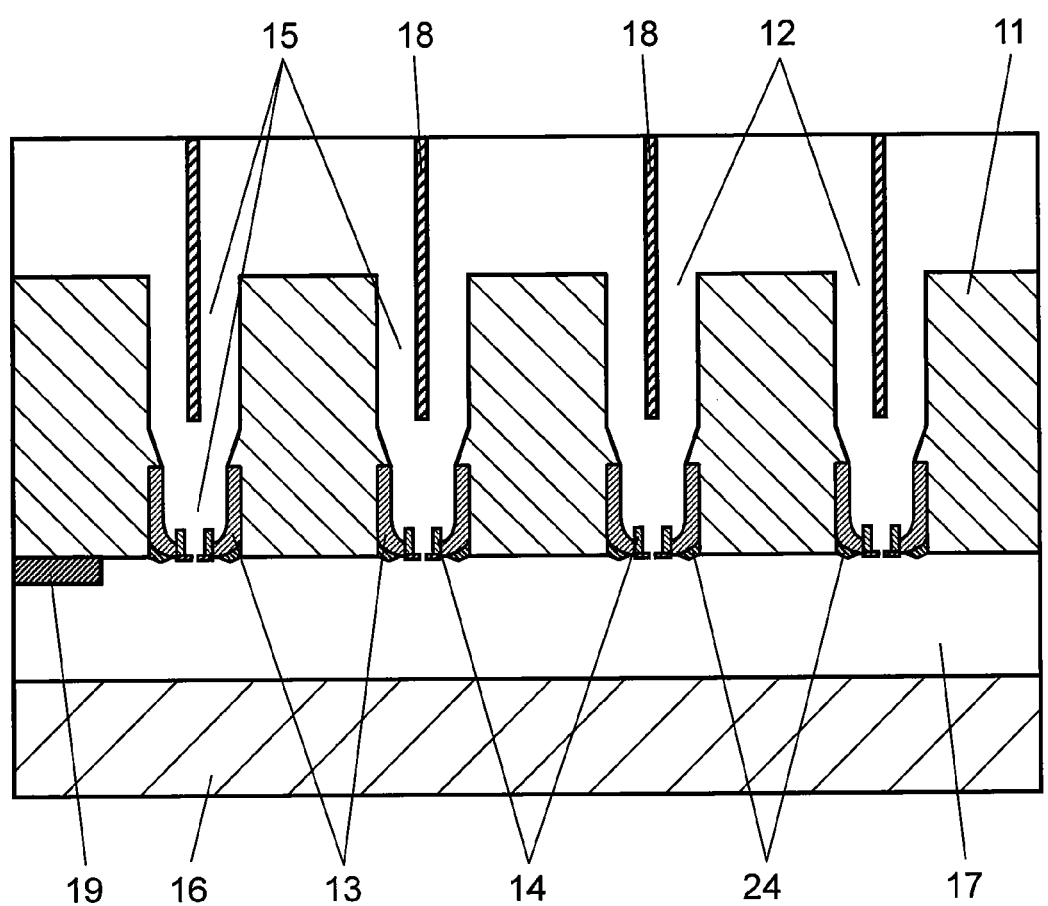
FIG. 1 is a sectional view showing a cell electrophysiological sensor in accordance with one exemplary embodiment of the present invention.

REFERENCE MARKS IN THE DRAWINGS 11 mounting substrate
12 through hole
13 glass tube
14 sensor chip
15 electrolytic bath
16 passage substrate
17 electrolytic bath
18 electrode
19 electrode
20 thin plate
21 frame body
22 cell trapping surface
23 conducting hole
24 adhesive agent
25 holding head
26 glass tube holding mechanism
27 burner
28 protrusion
29 metal tube
30 liquid
30a water droplet

DETAILED DESCRIPTION OF THE PREFERRED EMBODIMENT

Hereinafter, an exemplary embodiment of the present invention is described with reference to drawings. Note here that the present invention is not necessarily limited to the exemplary embodiment.

Exemplary Embodiment

Figure 2:
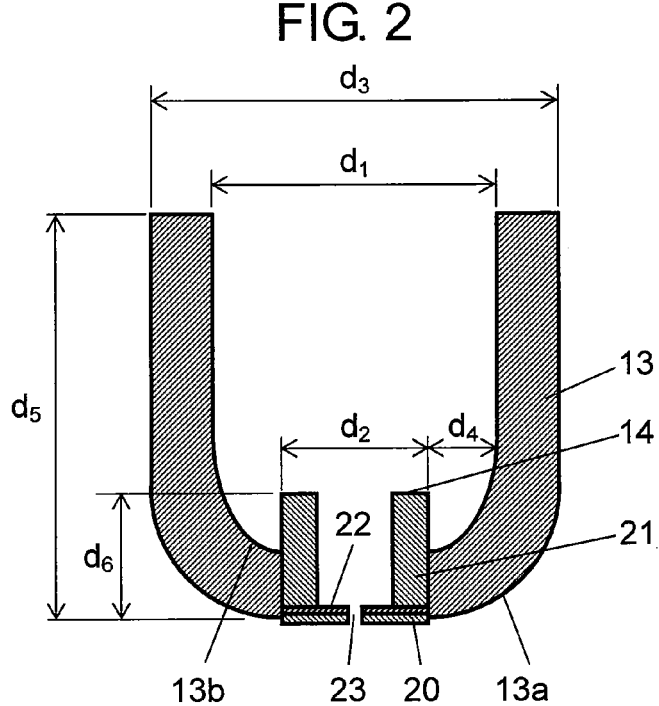
FIG. 2 is an enlarged sectional view showing a principal part of the cell electrophysiological sensor.

FIG. 1 is a sectional view showing a cell electrophysiological sensor in accordance with one exemplary embodiment of the present invention. FIG. 2 is an enlarged sectional view showing a principal part of the cell electrophysiological sensor. As shown in FIG. 1, the cell electrophysiological sensor of this exemplary embodiment includes mounting substrate 11, glass tube 13 inserted in through hole 12 of mounting substrate 11, and sensor chip 14 inserted in the lower end portion of glass tube 13.

The inside of glass tube 13 and the inside of through hole 12 of mounting substrate 11 are used as electrolytic bath 15. Passage substrate 16 is brought into contact with the lower part of mounting substrate 11. Space between passage substrate 16 and mounting substrate 11 is used as electrolytic bath 17.

In electrolytic baths 15 and 17, electrodes 18 and 19 are disposed, respectively. Electrodes 18 and 19 are electrically connected to electrolytic solutions filled in electrolytic baths 15 and 17.

Furthermore, as shown in FIG. 2, sensor chip 14 is composed of disc-shaped thin plate 20 and cylinder-shaped frame body 21 disposed on thin plate 20.

In this exemplary embodiment, sensor chip 14 is formed by dry etching a so-called SOI (Silicon On Insulator) substrate, in which both surfaces of a silicon dioxide layer are sandwiched by silicon layers.

That is to say, thin plate 20 is a laminated body of a silicon layer and a silicon dioxide layer, and frame body 21 is made of a silicon layer. That is to say, in this exemplary embodiment, cell trapping surface 22 on thin plate 20 is made of a silicon dioxide layer. In thin plate 20, conducting hole 23 is formed by dry etching. Electrolytic baths 15 and 17 shown in FIG. 1 can communicate with each other through conducting hole 23.

Furthermore, the thickness of thin plate 20 is set to 10 μm to 100 μm. The opening diameter of conducting hole 23 is set to 1 μm to 3 μmφ. The suitable opening diameter of conducting hole 23 is 5 μm or less for holding a cell.

Furthermore, it is desirable that glass tube 13 is made of highly hydrophilic glass having a contact angle with respect to water of not less than 0° and not more than 10°. Therefore, as a material of glass tube 13, glass containing silicon dioxide is preferred. An example of such glass may include borosilicate glass (Corning: #7052, #7056), aluminosilicate glass or lead borosilicate glass (Corning: #8161), or the like.

Note here that the contact angle with respect to water refers to an angle made by the surface of a water droplet and the surface of a solid in a state in which the water droplet of pure water is put on the solid surface and they reach equilibrium. In general, the contact angle can be measured by a θ/2 method. In the method, the contact angle can be determined from an angle of a line linking left and right end points to the top of the water droplet with respect to the surface of the solid. Alternatively, the angle can be measured by using a protractor, and the like.

Furthermore, as shown in FIG. 2, inner diameter d1 of glass tube 13 is larger than outer diameter d2 of sensor chip 14, and inner diameter d1 is set to 1400 μm. Outer diameter d3 of glass tube 13 is set to 2000 μm.

In this exemplary embodiment, length d4 between the inner side surface of glass tube 13 and the outer side surface of sensor chip 14 is set to about 0.05 mm to 0.4 mm. In this way, by providing a gap between glass tube 13 and sensor chip 14, it is possible to restrain sensor chip 14 and glass tube 13 from being brought into contact with each other before they are welded and being broken. Furthermore, length d5 of glass tube 13 is set to 2000 μm, which is longer than length d6 of sensor chip 14.

Furthermore, the softening point of glass is an important element from the viewpoint of workability. A temperature suitable for glass-welding glass tube 13 to the side surfaces of sensor chip 14 is not less than the softening point of glass. More preferably, the temperature is in the range from 500° C. to 900° C. The use of glass having a weldable temperature of less than 500° C. makes the intensity insufficient, and the use of glass having a weldable temperature of more than 900° C. lowers the workability.

Furthermore, when mounting substrate 11 and passage substrate 16 as shown in FIG. 1 are made of resin, they are easily molded and fabricated. Preferable materials include thermoplastic resin. Thus, a highly homogeneous molded product can be obtained from these materials with high productivity by using, for example, an injection molding method. More preferably, the thermoplastic resin may include any one of polycarbonate (PC), polyethylene (PE), olefin polymer, and poly(methyl methacrylate) acetate (PMMA), or the combination of two or more thereof. Mounting substrate 11 made of such materials can be easily bonded to glass tube 13 having an excellent hydrophilic property by using ultraviolet curing adhesive, agent 24 (FIG. 1). Further preferably, from the viewpoint of workability, production cost, and availability of materials, the thermoplastic resin may include cyclic olefin polymer, linear olefin polymer, or cyclic olefin copolymer obtained by polymerizing these polymers, or polyethylene (PE).

In particular, since the cyclic olefin copolymer is suitable for the production process and use environment of the present invention because it has excellent transparency and high resistance to alkaline and acidic inorganic agents. Furthermore, since these materials can transmit ultraviolet rays, they exhibit the effect when ultraviolet curing adhesive agent 24 is used.

With a method of mounting sensor chip 14 on mounting substrate 11 as in this exemplary embodiment, the cost is reduced and a yield is improved as compared with the case where entire mounting substrate 11 is formed of a silicon substrate and conducting hole 23 (FIG. 2) is directly provided in mounting substrate 11. In addition, in the case where defective conducting hole 23 is present in part, it can be repaired.

Next, an operation of the cell electrophysiological sensor of this exemplary embodiment is described. As shown in FIG. 1, an extracellular fluid is stored in electrolytic bath 15 of through hole 12 (including the inside of glass tube 13) of mounting plate 11, and an intracellular fluid is filled in electrolytic bath 17 at the lower side. Herein, the extracellular fluid is typically an electrolytic solution containing about 4 mM of $K^+$ ion, about 145 mM of $Na^+$ ion, and about 123 mM of $Cl^-$ ion in the case of, for example, mammalian muscle cells. The intracellular fluid is an electrolytic solution containing about 155 mM of $K^+$ ion, about 12 mM of $Na^+$ ion, and about 4.2 mM of $Cl^-$ ion.

In this state, between electrode 18 electrically connected to the extracellular fluid and electrode 19 electrically connected to the intracellular fluid, a conductive resistance value of about 100 kΩ to 10 MΩ can be observed. This is because the intracellular fluid or the extracellular fluid penetrates through conducting hole 23 (FIG. 2), so that an electric circuit is formed between two electrodes 18 and 19.

Next, a cell is put into electrolytic bath 15 located upside. Thereafter, when the pressure of electrolytic bath 17 located at the lower side is reduced, the cell is attracted to the opening part of conducting hole 23 so as to block the opening part of conducting hole 23. Thereby, the electric resistance between the extracellular fluid and the intracellular fluid becomes a sufficiently high as 1 GΩ or more (hereinafter, this state is referred to as "giga seal"). In the giga seal state, when the intracellular potential and extracellular potential change due to the electrophysiological activity of the cell, a slight potential difference or electric current can be measured with high accuracy.

Figure 3:
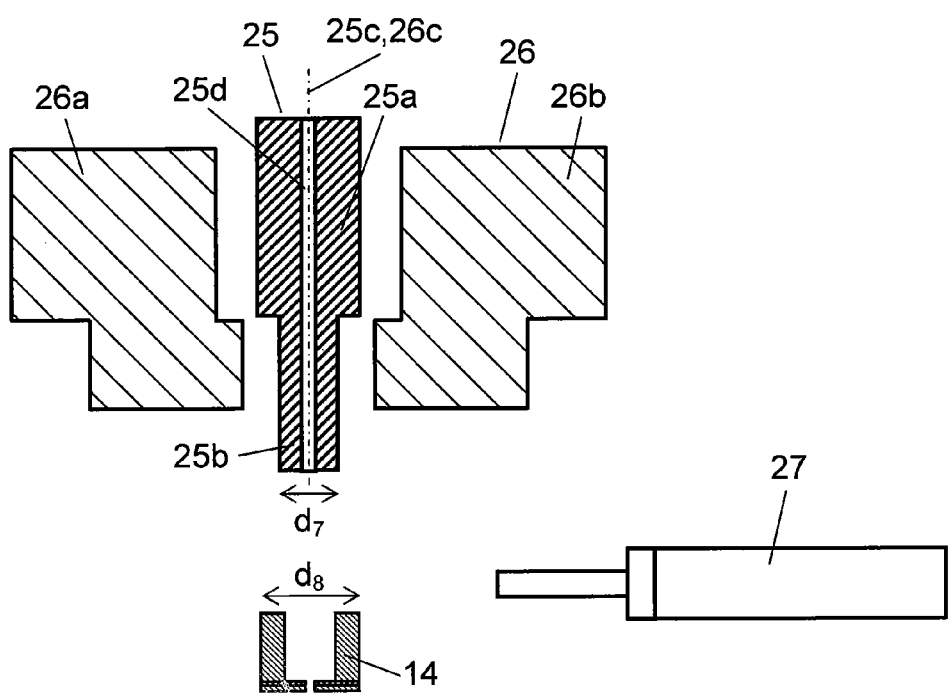
FIG. 3 is a schematic sectional view showing a production apparatus of the cell electrophysiological sensor.

Next, a production apparatus of a cell electrophysiological sensor in this exemplary embodiment is described with reference to FIG. 3. FIG. 3 is a schematic sectional view showing a production apparatus of the cell electrophysiological sensor in this exemplary embodiment. As shown in FIG. 3, the production apparatus includes holding head 25 for holding sensor chip 14 and glass tube holding mechanism 26 disposed on the outer periphery of holding head 25. Furthermore, the production apparatus includes a combustion device (burner 27) for locally applying a wind pressure to the side surface of glass tube 13 from the outside of glass tube 13 and melting glass tube 13. Holding head 25 and glass tube holding mechanism 26 have a function of rotating sensor chip 14 and glass tube 13 around vertical axes 25c and 26c as a center.

Note here that holding head 25 uses a mechanism that holds sensor chip 14 by adsorption in this exemplary embodiment although holding head 25 may be a mechanism that picks and holds the side surface of sensor chip 14. With the mechanism by adsorption, a stress load to micro-sensor chip can be reduced. Holding head 25 of this exemplary embodiment includes columnar-shaped base 25a and tip end portion 25b adjoining base 25a. Outer diameter d7 of tip end portion 25b is smaller than the outer diameter of base 25a. In the center of the columnar shape, suction hole 25d whose axis is columnar vertical axis 25c is formed. Sensor chip 14 is sucked by suction through suction hole 25d toward the upper part. The lower surface of tip end portion 25b is used as a surface for adsorbing sensor chip 14.

Similar to holding head 25, also glass tube holding mechanism 26 may be an adsorbing mechanism. However, since glass tube 13 has a larger outer dimension and higher mechanical strength as compared with sensor chip 14, this exemplary embodiment employs a chuck mechanism for sandwiching the side surface of glass tube 13. That is to say, glass tube holding mechanism 26 is composed of left holding part 26a and right holding part 26b. Left holding part 26a and right holding part 26b are disposed at the outer periphery of holding head 25. Space formed by left holding part 26a and right holding part 26b, that is, space surrounding holding head 25 forms columnar space having vertical axis 26c that coincides with vertical axis 25c that is a center of holding head 25. Left holding part 26a and right holding part 26b are movable toward left and right, respectively. Therefore, when left holding part 26a and right holding part 26b move in the direction approaching to vertical axis 26c, respectively, they hold glass tube 13. When left holding part 26a and right holding part 26b moves in the direction parting from vertical axis 26c, respectively, the holding of glass tube 13 is released.

Furthermore, in this exemplary embodiment, burner 27 capable of applying a wind pressure and flame at the same time is used as a combustion device. However, for example, a wind pressure generating device such as a motor capable of locally applying a wind pressure to the side surface of glass tube 13 from the outside of glass tube 13, and a heating device such as IH (Induction Heating), a heater, a laser for melting a glass tube may be used together. In this case, while a wind pressure is applied to the side surface of glass tube 13, the region in which the wind pressure is applied is heated. Thereby, glass tube 13 can be thermally deformed toward the inside as mentioned below.

Furthermore, in this exemplary embodiment, although flame is used in the glass welding step, hot air may be used. That is to say, the production apparatus may include, instead of burner 27, a hot air generating device capable of melting glass tube 13 while applying a wind pressure by hot air to the side surface of glass tube 13 from the outside of glass tube 13.

Such production apparatuses can deform glass tube 13 to be curved toward sensor chip 14 located inside by a wind pressure and heat. Thus, even when there is space between glass tube 13 and sensor chip 14, welding can be carried out easily Furthermore, this production apparatus is designed so that diameter d7 of the tip end of a smaller-diameter part of holding head 25, that is, a cross section of the surface for adsorbing sensor chip 14 is smaller than outer diameter d8 of sensor chip 14. This can restrain the molten glass from being attached to holding head 25.

In addition, both holding head 25 and glass tube holding mechanism 26 are formed of materials having high heat resistance so that they can withstand the heat in the glass welding step mentioned below. In particular, in this exemplary embodiment, holding head 25 is formed of a superalloy having higher thermal conductivity than that of glass tube holding mechanism 26, thus suppressing temperature unevenness of sensor chip 14 in the glass welding step. Furthermore, glass tube holding mechanism 26 is made of ceramic having a higher thermal insulation performance than that of holding head 25, thereby restraining an ambient temperature inside the apparatus from being decreased in the glass welding step.

Next, a production process of a cell electrophysiological sensor of this exemplary embodiment is described with reference to FIGS. 4A to 4H, 5A, and 5B. FIGS. 4A to 4H, 5A, and 5B are views showing a production process of a cell electrophysiological sensor in this exemplary embodiment.

Figure 4A:
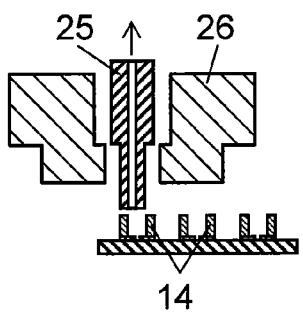
FIG. 4A is a view showing a production process of the cell electrophysiological sensor.

Firstly, in a step of adsorbing a chip, as shown in FIG. 4A, holding head 25 adsorbs and holds sensor chip 14 by sucking it through suction hole 25d in the direction shown by an arrow.

Figure 4D:
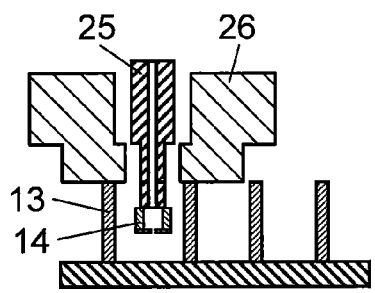
FIG. 4D is a view showing the production process of the cell electrophysiological sensor.
Figure 4G:
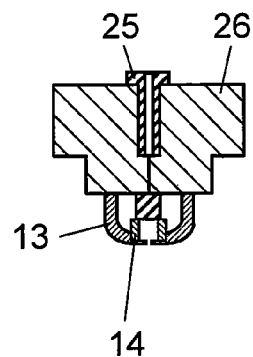
FIG. 4G is a view showing the production process of the cell electrophysiological sensor.
Figure 4B:
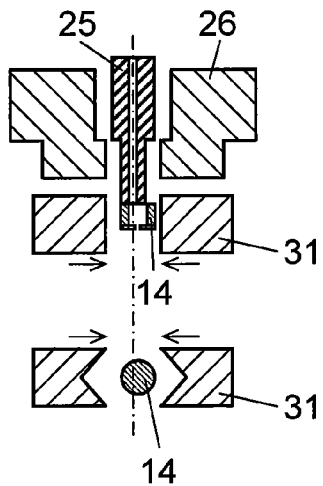
FIG. 4B is a view showing the production process of the cell electrophysiological sensor.
Figure 4E:
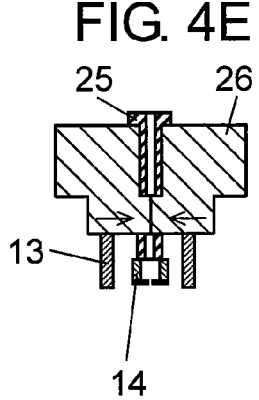
FIG. 4E is a view showing the production process of the cell electrophysiological sensor.
Figure 4H:
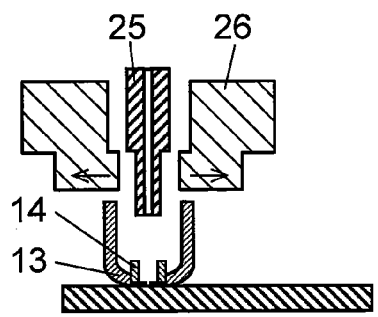
FIG. 4H is a view showing the production process of the cell electrophysiological sensor.
Figure 4C:
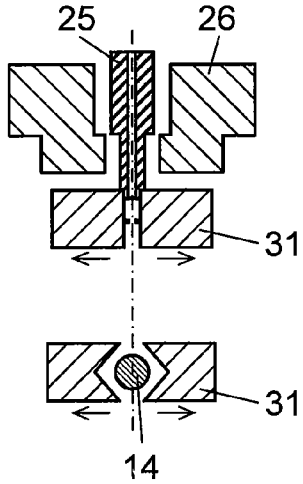
FIG. 4C is a view showing the production process of the cell electrophysiological sensor.

Next, in a centering step, as shown in FIGS. 4B and 4C, centering is carried out so that sensor chip 14 is located in the center of holding head 25 in a state in which sensor chip 14 is adsorbed and held. FIG. 4B shows a side view of glass tube holding mechanism 26 and a plan view thereof in the upper and lower parts, respectively. Similarly, FIG. 4C shows a side view of glass tube holding mechanism 26 and a plan view thereof in the upper and lower parts, respectively. That is to say, in the centering step, as shown in FIG. 4B, centering mechanism 31 sandwiches sensor chip 14 adsorbed and held by holding head 25 between the left and right sides. Herein, centering mechanism 31 is disposed in such a way in which its vertical axis coincides with the vertical axis of holding head 25 and glass tube holding mechanism 26. Thus, as shown in FIG. 4C, sensor chip 14 is centered and held so that its vertical axis coincides with the vertical axis of holding head 25 and glass tube holding mechanism 26. Thereafter, as shown by the arrow in FIG. 4C, centering mechanism 31 is removed by moving it to the left and right sides. This corresponds to a step of holding sensor chip 14.

Thereafter, in a chucking step, as shown in FIG. 4D, holding head 25 holding sensor chip 14 is inserted into arranged glass tube 13. Thereafter, as shown in FIG. 4E, glass tube holding mechanism 26 holds glass tube 13. This corresponds to a step of holding glass tube 13.

Note here that the step of holding glass tube 13 may be carried out before the step of holding sensor chip 14. However, in this exemplary embodiment, glass tube 13 is held after the step of holding sensor chip 14. According to this order, sensor chip 14 is not likely to be broken and the positions of the glass tube and the sensor chip can be kept in the center.

Figure 4F:
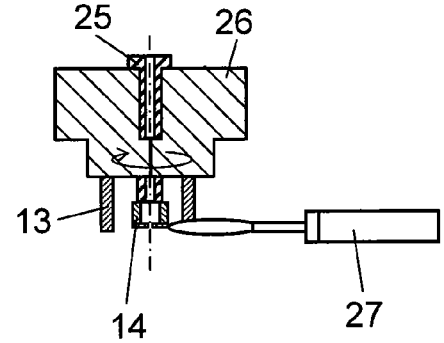
FIG. 4F is a view showing the production process of the cell electrophysiological sensor.

Next, in a glass welding step, as shown in FIG. 4F, burner 27 is directed to the side surface of the bottom end portion of glass tube 13 from the outside of glass tube 13, and strongly emits flame in substantially parallel to the horizontal section of glass tube 13 (that is, in parallel to thin plate 20 in FIG. 2O). At this time, by using the rotating function of holding head 25 and glass tube holding mechanism 26, sensor chip 14 and glass tube 13 are rotated around the vertical axis of sensor chip 14 in the direction shown by an arrow. Thus, although a single burner 27 is used and flame is emitted from a single direction, sensor chip 14 can be welded in a 360-degree direction easily and uniformly. This corresponds to a step of melting glass tube 13 to be glass-welded to the side surface of sensor chip 14.

In this exemplary embodiment, since both frame body 21 (FIG. 2) of sensor chip 14 and glass tube 13 have a cylindrical shape, uniform heating and uniform welding can be carried out.

Herein, in this exemplary embodiment, since burner 27 is used, strong and concentrated flame can be emitted. Therefore, as shown in FIG. 4G, the lower end of glass tube 13 with which the flame is bought in direct contact is melted to be curved toward the inside (toward sensor chip 14 side) with the power of the flame. Thus, even when inner diameter d1 (FIG. 2) of glass tube 13 is larger than the outer diameter d2 (FIG. 2) of sensor chip 14, glass tube 13 and sensor chip 14 can be bonded to each other in a state in which they are brought into close contact with each other.

Thereafter, in an installing step, as shown in FIG. 4H, an integrated product of sensor chip 14 and glass tube 13 is installed.

Figure 5A:
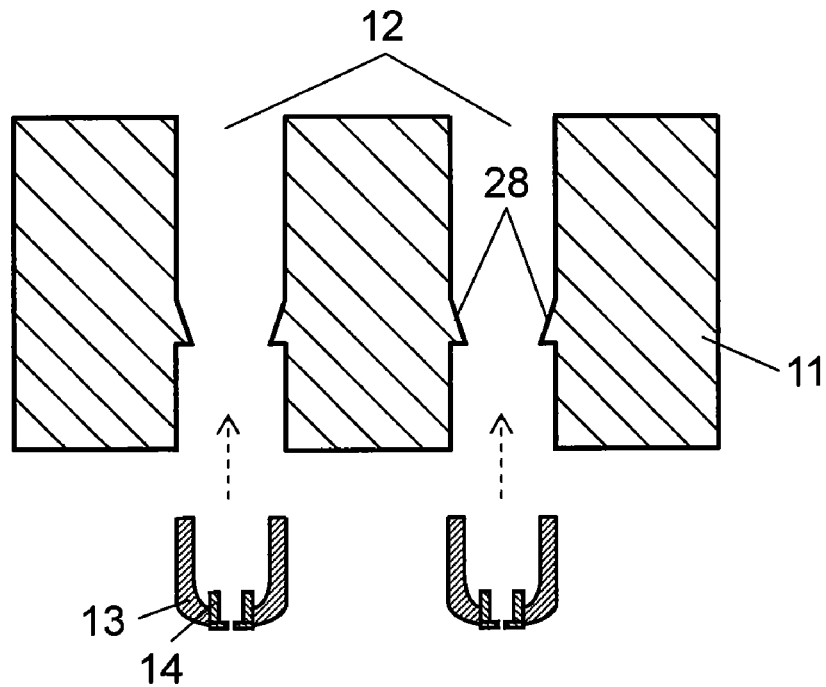
FIG. 5A is a view showing a production process of the cell electrophysiological sensor.
Figure 5B:
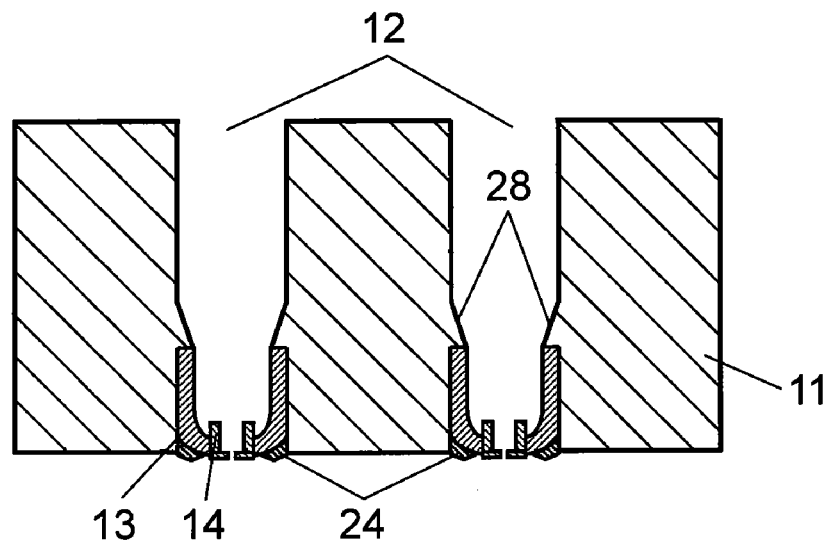
FIG. 5B is a view showing the production process of the cell electrophysiological sensor.

Then, the integrated product of sensor chip 14 and glass tube 13 is inserted into through hole 12 of mounting substrate 11 as shown in FIG. 5A, and bonded with, for example, adhesive agent 24 as shown in FIG. 5B. Thus, the cell electrophysiological sensor of this exemplary embodiment can be produced. In this exemplary embodiment, since protrusion 28 is provided on the inner wall of through hole 12, glass tube 13 can be positioned easily.

Figure 6A:
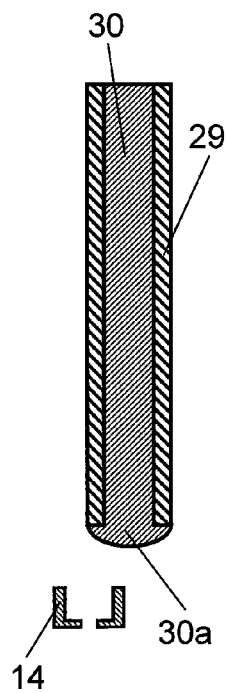
FIG. 6A is a sectional view to illustrate a step in another adsorbing method in the production process.
Figure 6B:
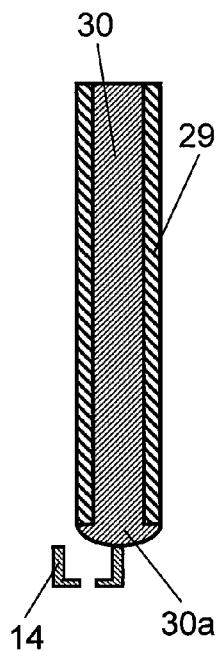
FIG. 6B is a sectional view to illustrate a step in the other adsorbing method in the production process.
Figure 6C:
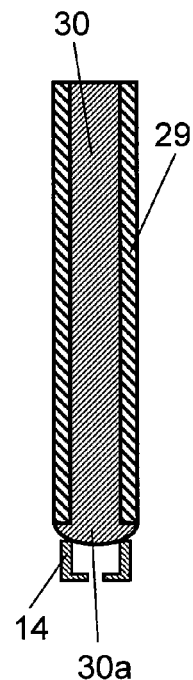
FIG. 6C is a sectional view to illustrate a step in the other adsorbing method in the production process.

Next, another production process in which adsorption and centering of sensor chip 14 are carried out efficiently is described with reference to drawings. FIGS. 6A to 6C are sectional views to illustrate steps in another adsorbing method in the production process.

Firstly, as shown in FIG. 6A, heat resistant hollow metal tube 29 made of, for example, stainless steel is prepared. Liquid 30 such as water having a predetermined surface tension is filled in the hollow part of metal tube 29 so as to form water droplet 30a on the tip end portion of metal tube 29 while the pressure is controlled. In order to do so, it is preferable that liquid 30 is filled in hollow metal tube 29 and that a valve control unit for keeping the inside of the hollow part to be in a reduced-pressure state.

Furthermore, it is preferable that a water droplet size (in particular, width dimension) of water droplet 30a is larger than the shape of sensor chip 14. Then, in order to form a water droplet 30a on the tip end of metal tube 29, it is preferable that a metal material capable of easily being processed into a hollow shape is used. Furthermore, since glass welding is carried out in the later step, heat resistant materials or materials stable at high temperatures, for example, ceramic materials or heat-resistant glass can be used.

Next, as shown in FIG. 6B, when sensor chip 14 is brought into contact with the surface of water droplet 30a, sensor chip 14 is adsorbed by water droplet 30a by a surface tension.

Thereafter, as shown in FIG. 6C, sensor chip 14 that is brought into contact with the surface of water droplet 30a is attracted to the center part of the tip end of water droplet 30a formed in a spherical shape by a surface tension of water droplet 30a.

As mentioned above, the position of holding sensor chip 14 attracted by water droplet 30a formed on the tip end portion of metal tube 29 is attracted to substantially the center part of the tip end of water droplet 30a. This is determined by the results obtained by repeating experiments of FIGS. 6A to 6C. Thus, sensor chip 14 can be adsorbed in a state in which sensor chip 14 and metal tube 29 have the same central axis.

Therefore, by forming water droplet 30a on the tip end portion of hollow metal tube 29 having a predetermined dimension and by using an adsorbing method using the surface tension of water droplet 30a, the adsorption and centering of sensor chip 14 can be easily carried out via water droplet 30a. Thereafter, liquid 30 and water droplet 30a that present inside hollow metal tube 29 are removed by carrying out vacuum suction by a valve operation, and the like. In addition to this, the inside of the hollow is kept at a reduced-pressure state, thereby achieving a state in which sensor chip 14 is vacuum adsorbed to the center part of the tip end of metal tube 29.

After sensor chip 14 is adsorbed in this way, the production process later than the step shown in FIG. 4D is carried out. Thus, it is possible to produce a cell electrophysiological sensor that is disposed in the predetermined position. According to the production process and the production apparatus of adsorbing sensor chip 14 while centering is carried out by using a water droplet, micro-sensor chip 14 can be held without loading a mechanical stress to sensor chip 14. Therefore, it is possible to provide a production process capable of remarkably reducing structural defects such as breakage or crack in sensor chip 14. Furthermore, the process and apparatus of adsorbing while centering by using a water droplet can be applied to the case other than sensor chip 14 of the cell electrophysiological sensor in this exemplary embodiment. For example, they can be applied to cases on which sensor chips of various sensors such as a DNA micro array, a protein sensor, a sugar sensor, or other micro devices are mounted. In particular, when a micro device is intended to be handled in ambient atmosphere, forces generated by static electricity, mechanical contact with a jig, and the like, make it extremely difficult to install or move the device to a desired position. On the other hand, in the production process using a water droplet, a force from the outer pressure generated at the time of handling can be reduced. Therefore, in particular, the production process is effective when a sensor chip or a device provided with a hydrophilic property is handled, because centering and adsorption can be carried out easily.

As described above, the use of the production process and the production apparatus of this exemplary embodiment makes it possible to produce a cell electrophysiological sensor with high measurement accuracy. This is because this exemplary embodiment makes it possible to form sensor chip 14 in which air bubbles are less likely to be deposited in the vicinity of conducting hole 23 of sensor chip 14.

That is to say, when the production process and the production apparatus of this exemplary embodiment are used, as shown in FIG. 1, highly hydrophilic glass tube 13 can be intervened in the outer periphery of sensor chip 14, that is, space between through hole 12 of mounting substrate 11 and sensor chip 14 in this exemplary embodiment. Therefore, air bubbles generated in the periphery of sensor chip 14, that is, inside through hole 12 can be reduced. Therefore, air bubbles deposited in the vicinity of the opening of conducting hole 23 can be reduced. As a result, it is possible to produce a cell electrophysiological sensor with high measurement accuracy.

Furthermore, in this exemplary embodiment, the upper part of sensor chip 14 is surrounded by glass tube 13. This can restrain air bubbles from covering the upper part of sensor chip 14.

Figure 9:
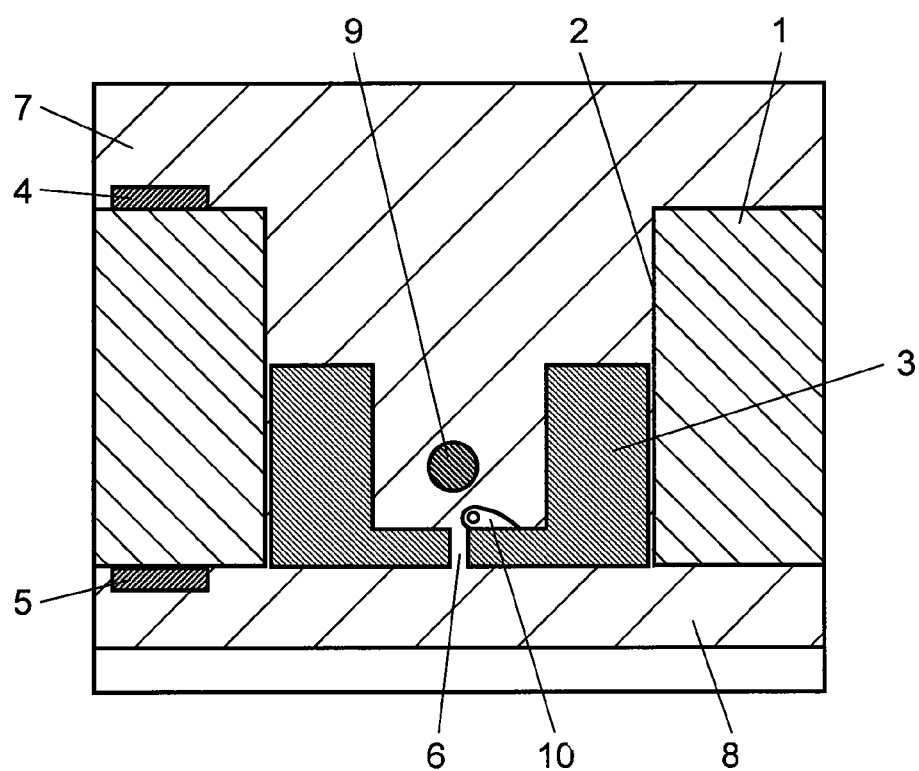
FIG. 9 is a sectional view showing a conventional cell electrophysiological sensor.

In other words, in a conventional configuration shown in FIG. 9, sensor chip 3 is surrounded by the inner wall of through hole 2. Conventionally, sensor chip 3 and the inner walls of through hole 2 are made of hydrophobic materials. Therefore, when an electrolytic solution is filled, the entire inside of the frame body may be covered with air bubbles from the upper part of sensor chip 3, thus making it impossible to carry out measurement.

On the other hand, in sensor chip 14 produced in this exemplary embodiment, since the upper part of sensor chip 14 is surrounded by hydrophilic glass tube 13, it is possible to restrain air bubbles from covering the upper part of sensor chip 14.

Furthermore, in this exemplary embodiment, the outer periphery of micro-sensor chip 14 is closely fixed by glass tube 13 having a larger outer diameter. Therefore, since sensor chip 14 together with glass tube 13 can be mounted on mounting substrate 11, mounting can be carried out easily. As compared with the case in which the outer diameter of sensor chip 14 made of silicon is increased, when cheap glass tube 13 is used, cost for material can be reduced.

Furthermore, since glass tube 13 and sensor chip 14 are bonded to each other by glass welding, large bonding strength and high airtightness can be achieved. Therefore, an electrolytic solution can be restrained from flowing into space between glass tube 13 and sensor chip 14, thus contributing to reduction of leakage current. That is to say, the use of the production process and the production apparatus of this exemplary embodiment makes it possible to produce a cell electrophysiological sensor with high measurement accuracy.

Furthermore, according to this exemplary embodiment, flame is strongly emitted in parallel to the horizontal surface of glass tube 13. Therefore, the flame is concentrated on the bottom end portion of glass tube 13, so that the outside of surface 13*a* (FIG. 2) of the bottom end portion is curved toward the inside. Thus, glass tube 13 can be easily inserted into the inside of through hole 12 of mounting substrate 11.

Furthermore, according to this exemplary embodiment, inner wall 13*b* (FIG. 2) of the bottom end portion of glass tube 13 is also curved toward the inside. With such a curved shape, air bubbles are less likely to be generated as compared with the case in which corner portions are formed.

Furthermore, according to this exemplary embodiment, by using burner 27, flame can be strongly emitted and locally directed. Therefore, even when there is space between glass tube 13 and sensor chip 14, a part of glass tube 13 can be drawn to sensor chip 14 side with the use of the power of the flame.

Furthermore, although flames may be emitted from many directions at one time, it is preferable that burner 27 is installed in a single region and flame is emitted from a single direction as in this exemplary embodiment.

That is to say, when burners 27 are used from many directions, hot air by the flame is interfered with each other, thus weakening the power of the flame. As a result, it becomes difficult to curve glass tube 13 toward the inside.

In this exemplary embodiment, although hot air is generated by using burner 27, air can be also generated by using, for example, a motor. Also in this case, it is more desirable that the air is generated toward the side surface of glass tube 13 from a single direction because when the air is generated from many directions, a wind pressure may be reduced by the interference.

When space between glass tube 13 and sensor chip 14 is small, however, glass tube 13 and sensor chip 14 can be bonded to each other easily with a low wind pressure. Therefore, a large number of burners 27 may be used. In this case, when burners 27 are disposed in a radial manner, uniform welding can be carried out. When a large number of burners 27 are used, welding time can be shortened.

Figure 7:
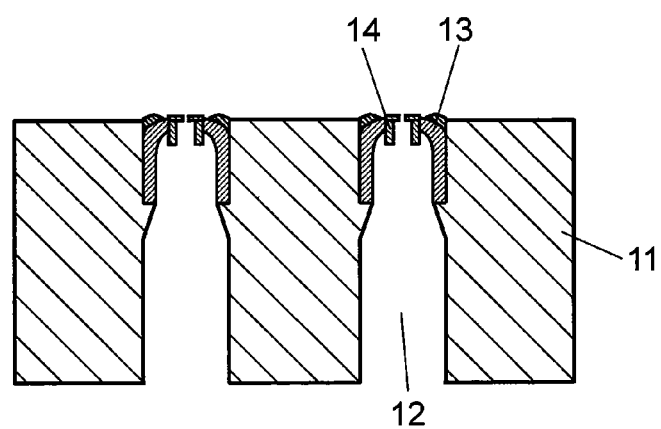
FIG. 7 is a sectional view showing another cell electrophysiological sensor in accordance with one exemplary embodiment of the present invention.
Figure 8:
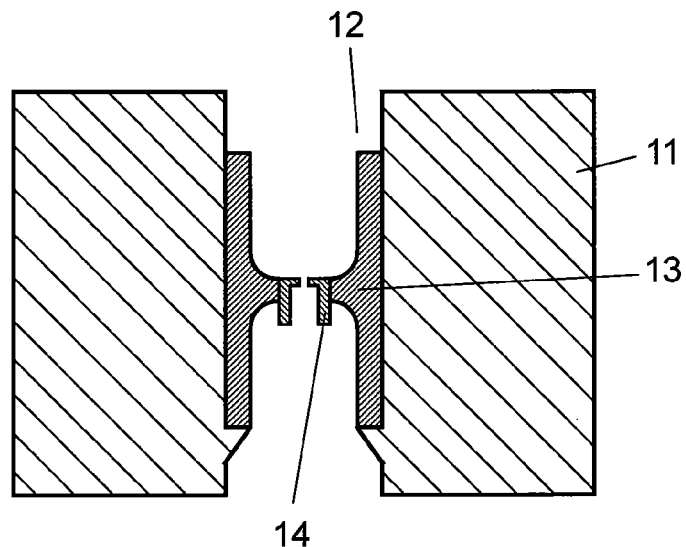
FIG. 8 is a sectional view showing still another cell electrophysiological sensor in accordance with the exemplary embodiment.

In this exemplary embodiment, sensor chip 14 is inserted into bottom end portion of the glass tube 13. However, as shown in FIG. 7, sensor chip 14 may be inserted into the upper end portion. Alternatively, as shown in FIG. 8, sensor chip 14 may be inserted into the center part. In such cases, glass tube 13 is located in the lower part of sensor chip 14, and the inside of glass tube 13 can be used as a lower side electrolytic bath. Therefore, it is possible to restrain air bubbles from being deposited in the vicinity of the outlet of conducting hole 23. Consequently, when a cell is sucked by reducing the pressure in electrolytic bath 17 (FIG. 1), it is possible to prevent the phenomenon the pressure cannot be transferred to the upper part by air bubbles. Furthermore, it is possible to restrain the inhibition of electric conduction between the upper part and the lower part of conducting hole 23 (FIG. 2). As a result, the measurement accuracy of the cell electrophysiological sensor is improved.

Note here that sensor chip 14 may be disposed upside down. However, since a SOI substrate is used in this exemplary embodiment, it is preferable that sensor chip 14 is disposed in such a direction that a silicon dioxide layer is used as cell trapping surface 22 (FIG. 2). That is to say, since a silicon dioxide layer has a higher insulation property as compared with a silicon layer, leakage current via sensor chip 14 can be reduced.

Industrial Applicability

The present invention makes it possible to efficiently produce a cell electrophysiological sensor with high measurement accuracy and is useful in producing cell electrophysiological sensors.

The invention claimed is:

1. A production process of a cell electrophysiological sensor, comprising:
providing a sensor chip;
surrounding an outer periphery of a side surface of the sensor chip with a glass tube;
applying pressurized gas to a side surface of the glass tube from an outside of the glass tube, and melting the glass tube to be glass-welded to the side surface of the sensor chip.

2. The production process of a cell electrophysiological sensor of claim 1,
wherein the providing of a sensor chip comprises: forming a spherical-shaped water droplet on a tip end of a cylindrical or bar-shaped holder; bringing the sensor chip into contact with a surface of the water droplet; and holding the sensor chip in a state in which the sensor chip is arranged in a center part of the tip end of the holder with a surface tension of the water droplet.

3. The production process of a cell electrophysiological sensor of claim 1,
wherein the glass welding comprises emitting flame to the side surface of the glass tube from the outside of the glass tube, thereby glass-welding the glass tube to the side surface of the sensor chip.

4. The production process of a cell electrophysiological sensor of claim 1,
wherein a direction of the pressurized gas in the glass welding is a single direction.

5. The production process of a cell electrophysiological sensor of claim 1,
wherein the glass welding includes emitting flame to the side surface of the glass tube from a single direction.

6. The production process of a cell electrophysiological sensor of claim 1,
wherein the glass welding includes curving the glass tube toward an inside.

7. The production process of a cell electrophysiological sensor of claim 1,
wherein the glass welding includes rotating the glass tube and the sensor chip disposed inside the glass tube around a vertical axis of the sensor chip as a center.

8. The production process of a cell electrophysiological sensor of claim 1, wherein after the providing of the sensor chip, the glass tube is held.

* * * * *

UNITED STATES PATENT AND TRADEMARK OFFICE
CERTIFICATE OF CORRECTION

PATENT NO. : 8,375,745 B2  
APPLICATION NO. : 12/808499  
DATED : February 19, 2013  
INVENTOR(S) : Hiroshi Ushio et al.

Page 1 of 1

It is certified that error appears in the above-identified patent and that said Letters Patent is hereby corrected as shown below:

On the Title Page

At Item (56), FOREIGN PATENT DOCUMENTS, delete duplicate entries:

"JP  2007-174990 A  7/2007" and "WO  WO 2007-119772 A1  10/2007".

Signed and Sealed this  
Twenty-third Day of April, 2013

Teresa Stanek Rea  
*Acting Director of the United States Patent and Trademark Office*